(12) United States Patent
Ohta

(10) Patent No.: US 8,673,376 B2
(45) Date of Patent: Mar. 18, 2014

(54) POLYPHENOL-CONTAINING COMPOSITION FOR ORAL ADMINISTRATION OR EXTERNAL USE AND USE OF SAME

(75) Inventor: Tomihisa Ohta, Kanazawa (JP)

(73) Assignee: Biotherapy Development Research Center Co., Ltd., Kanazawa-shi Ishikaw (JP)

( * ) Notice: Subject to any disclaimer, the term of this patent is extended or adjusted under 35 U.S.C. 154(b) by 0 days.

(21) Appl. No.: 13/386,147

(22) PCT Filed: Jul. 21, 2010

(86) PCT No.: PCT/JP2010/062275
§ 371 (c)(1),
(2), (4) Date: Apr. 13, 2012

(87) PCT Pub. No.: WO2011/010678
PCT Pub. Date: Jan. 27, 2011

(65) Prior Publication Data
US 2012/0189724 A1 Jul. 26, 2012

(30) Foreign Application Priority Data
Jul. 21, 2009 (JP) .................................. 2009-170353

(51) Int. Cl.
*A61K 36/73* (2006.01)
*A61K 36/00* (2006.01)

(52) U.S. Cl.
USPC ......................................... 424/765; 424/725

(58) Field of Classification Search
None
See application file for complete search history.

(56) References Cited

U.S. PATENT DOCUMENTS

2009/0047305 A1   2/2009   Tanaka et al.

FOREIGN PATENT DOCUMENTS

| JP | 2000-16951 A | 1/2000 |
| JP | 2000-60482 A | 2/2000 |
| JP | 2002-153240 A | 5/2002 |
| JP | 2002-335911 A | 11/2002 |
| JP | 2004-115466 A1 | 4/2004 |
| JP | 2006-111597 A | 4/2006 |
| JP | 2006-511509 A | 4/2006 |
| JP | 2007-176858 A | 7/2007 |

OTHER PUBLICATIONS

Williams et al, Isolation and identification of kaempferol and quercetin from strawberries. Journal of the American Chemical Society (1952), 74, 5919-20.*
Wilkinson et al, Freeze-dried strawberry powder lowers total cholesterol and LDL-cholesterol in females with abdominal adiposity and dyslipidemia. The FASEB Journal, (2009) vol. 23, No. S1. Abstract No. 563.8. Meeting Info: Experimental Biology 2009 (EB 2009.*
Takada et al, Ellagic acid. Cosmetic Science and Technology Series (2005), 27(Microbial Enzymes and Biotransformations (2nd Edition)), 511-521.*
Oct. 12, 2010, International Search Report.
China Patent Office, Office Action, 201080042124.6 (corresponding application in China), mailed Mar. 12, 2013 (English Translation).
Chinese Office Action (English Translation) Corresponding to Application No. 201080042124.6.

* cited by examiner

*Primary Examiner* — Qiuwen Mi
(74) *Attorney, Agent, or Firm* — Hogan Lovells US LLP

(57) ABSTRACT

A composition including a strawberry-derived polyphenol highly effective for oral administration or external use. A composition for oral administration or external use is obtained by subjecting a hot water extract of strawberry to adsorption chromatography using an aromatic synthetic absorbent, removing the fractions passing through the column and fractions eluted with water, and then eluting with a 5 to 60% aqueous ethanol solution.

4 Claims, 14 Drawing Sheets

POLYPHENOL-CONTAINING COMPOSITION FOR ORAL ADMINISTRATION OR EXTERNAL USE AND USE OF SAME

This application is the U.S. National Phase under 35 U.S.C. §371 of International Application PCT/JP2010/062275, filed on Jul. 21, 2010, which claims priority to Japanese Patent Application No. 2009-170353, filed on Jul. 21, 2009; the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a composition containing a strawberry-derived polyphenol for oral administration or external use, and specifically to a food composition, a pharmaceutical composition, and a cosmetic composition containing a strawberry-derived polyphenol.

BACKGROUND ART

Strawberry contains vitamin C, ellagic acid, anthocyanin, quercetin, kaempferol, citric acid, and malic acid. Patent Document 1 describes a composition which prevents and improves obesity, the composition containing a strawberry-derived anthocyanidin. According to the document, the extract with a high purity of 90% or more of the anthocyanidin compound (dye component) was prepared by extracting strawberry with water at 4° C. to obtain an extract, passing the extract through a column filled with a synthetic adsorption resin (HP20), which is an aromatic synthetic absorbent, thereby adsorbing the dye component on the column, passing water through the column for washing, and passing a 70% aqueous ethanol solution thereby eluting the dye component adsorbed on the column, and removing the solvent from the solution thus obtained.

It is also known that pectin is used as a dietary fiber component added to health food (Patent Document 2).

Patent document 1: Japanese Unexamined Patent Application Publication No. 2002-153240, claims 1, 2, and paragraphs 0033 to 0037

Patent Document 2: Japanese Unexamined Patent Application Publication No. 2007-330124, claim 9

DISCLOSURE OF THE INVENTION

Problems to be Solved by the Invention

The inventors carried out a dedicated research on the method for obtaining polyphenol from a hot water extract of strawberry, and have found that polyphenol is adsorbed on an aromatic synthetic absorbent, and obtained from a fraction eluted with a 5 to 60% aqueous ethanol solution, and that the constitution and activity of the component thus obtained vary according to the ethanol concentration.

The present invention is intended to provide a highly safe and highly effective composition containing a strawberry-derived polyphenol.

Means for Solving the Problem

The aspects of the present invention are described below.

(1) A composition for oral administration or external use, containing a fraction obtained by subjecting a hot water extract of strawberry to adsorption chromatography using an aromatic synthetic absorbent, removing the fractions passing through the column and fractions eluted with water, and then eluting with a 5 to 60% aqueous ethanol solution.

(2) The composition of (1), containing a fraction obtained by removing the fractions passing through the column and fractions eluted with water, and then eluting with a 5 to 15% aqueous ethanol solution.

(3) The composition of (1), containing a fraction obtained by removing the fractions passing through the column and fractions eluted with water and fractions eluted with a less than 40% aqueous ethanol solution, and then eluting with a 40 to 60% aqueous ethanol solution.

(4) The composition of any one of (1) to (3), further containing a polysaccharide thickener.

(5) A composition containing a strawberry-derived polyphenol and a polysaccharide thickener.

(6) The composition of any one of (1) to (5), which is a food composition, a pharmaceutical composition, or a cosmetic composition.

(7) The composition of (6), which is an anti-obesity composition.

(8) The composition of (6), which is an anti-inflammatory composition.

(9) The composition of (6), which is a melanin production inhibitor composition.

(10) The composition of any one of (4) to (9), wherein the polysaccharide thickener is strawberry-derived pectin.

Advantageous Effect of the Invention

The composition of the present invention is highly safe and highly effective.

EXPLANATION OF REFERENCES

Figure 1:
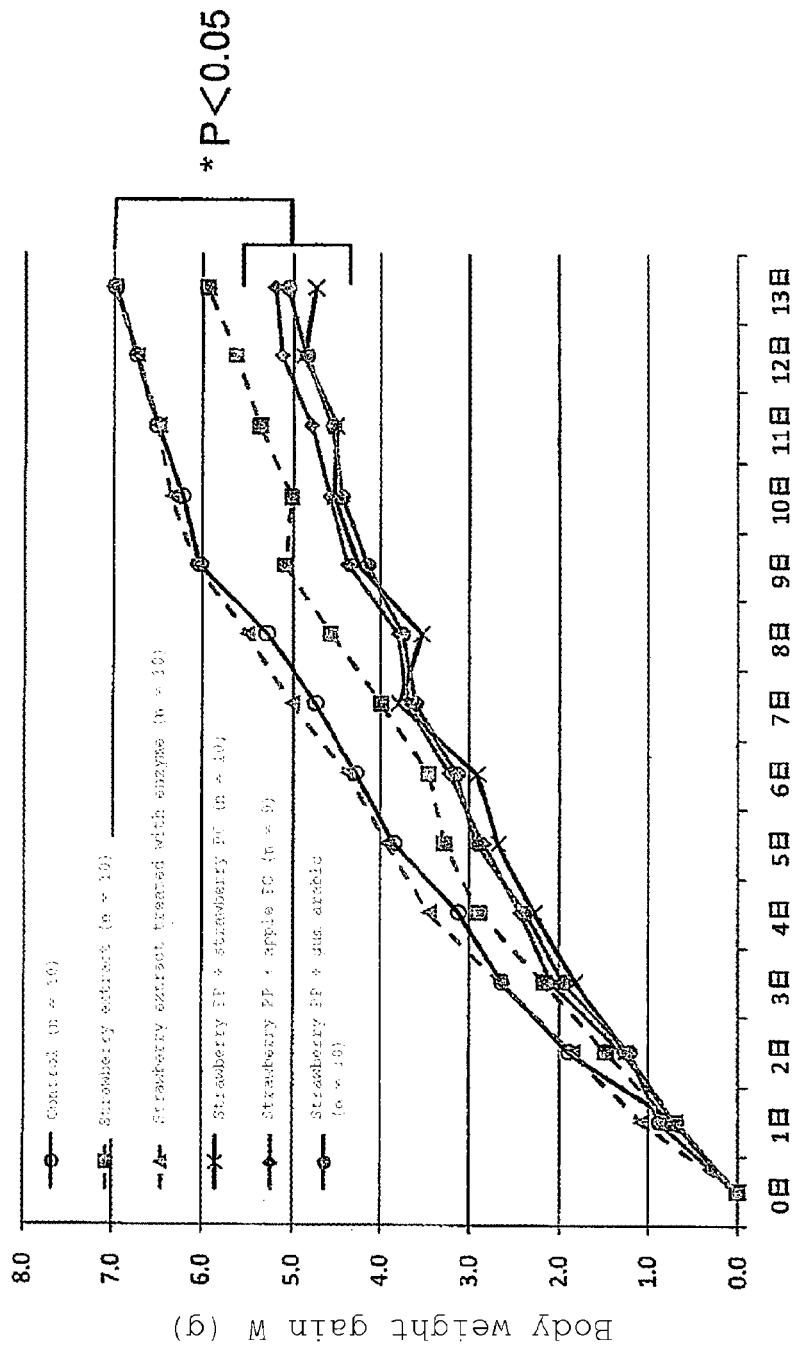
FIG. 1 is a graph showing the body weight gain after initiation of sample administration.

PP: polyphenol
PC: pectin

BEST MODE FOR CARRYING OUT THE INVENTION

In the present invention, the type of strawberry (scientific name: Fragaria L.) used as the source of a polyphenol is not particularly limited, and preferred examples include Holland strawberry (scientific name: Fragaria ananassa, English name: garden strawberry), and its varieties include Tochiotome, Danner, Aiberry, Amaou, Momoichigo, Akihime, Sagahonoka, Asuka Ruby, Toyonoka, Hokowase, Fukuba, Nyoho, Kurume No. 49, Tochinomine. Among them, Tochiotome is preferred. Examples of strawberry parts include fruits, leaves, stems, and roots, and among them, fruits are preferred herein.

In the present invention, the strawberry-derived polyphenol is preferably the fraction obtained by subjecting a hot water extract of strawberry to adsorption chromatography using an aromatic synthetic absorbent, removing the fractions passing through the column and fractions eluted with water, and then eluting with a 5 to 60% aqueous ethanol solution.

When the composition of the present invention is used as a composition for external use such as a cosmetic composition, from the viewpoints of melanin production inhibitory activity and tyrosinase inhibitory activity, the above-described fraction is preferably obtained by removing the fractions passing through the column and fractions eluted with water, and then eluting with a 5 to 15% aqueous ethanol solution. On the other hand, when used as a composition for oral administration, from the viewpoint of activity, in normal cases, the above-described fraction is preferably obtained by removing the fractions passing through the column and the fractions eluted with water and a less than 40% aqueous ethanol solution, and then eluting with a 40 to 60% aqueous ethanol solution.

The fraction is optionally further purified, and used as a strawberry-derived polyphenol.

The extracting solvent used to extract a polyphenol from strawberry is preferably hot water (water at 90 to 100° C.), thereby improving the yield of the polyphenol and pectin.

The aromatic synthetic absorbent used in the present invention is a synthetic substance with a porous structure having no ion exchange group, and used mainly for separation and purification of organic substances for its hydrophobic interaction. Various types of the absorbent are known, and examples thereof include those described in Japanese Patent No. 2784627, 3527661, and 3891746. Specific examples include aromatic synthetic absorbents produced by polymerizing styrene with divinylbenzene, and examples of commercial products include DIAION™ HP20, HP21, SEPABEADS™ SP825L, SP850, SP700, SP70 (manufactured by Mitsubishi Chemical Corporation or Nippon Rensui Co.), AMBERITE™ XAD2, XAD4, XAD16 (manufactured by Rohm and Haas, United States.).

The composition of the present invention contains a strawberry-derived polyphenol, and further contains a polysaccharide thickener, thereby improving its effects such as anti-obesity effect.

The polysaccharide thickener is not particularly limited, and examples thereof include pectin, gum arabic, guar gum, pullulan, sodium alginate. Among them, pectin and gum arabic are preferred.

The pectin is not particularly limited, and is preferably strawberry-derived pectin.

The strawberry-derived pectin may be prepared by subjecting a hot water extract of strawberry to adsorption chromatography using an aromatic synthetic absorbent, dissolving the fractions passing through the column and fractions eluted with water in an aqueous ethanol solution, preferably a 60 to 80% aqueous ethanol solution, and then filtering and washing the deposited insoluble matter with a 60 to 80% aqueous ethanol solution. The product may be used as it is or after further purification.

When the composition of the present invention contains a strawberry-derived polyphenol and a polysaccharide thickener, in normal cases, the mass ratio between the strawberry-derived polyphenol and polysaccharide thickener is preferably from 1:0.6 to 1:2.

The composition of the present invention has anti-obesity effect, interleukin 8 production inhibitory effect, and melanin production inhibitory effect, and is useful as a food composition, a pharmaceutical composition, or a cosmetic composition for preventing obesity, inflammation, or melanin production.

The composition of the present invention contains a strawberry-derived polyphenol and optionally a polysaccharide thickener, and may be combined with a known carrier for food use, medical use, or cosmetic use to make a formulation. When the composition of the present invention is used for oral administration, in normal cases, it takes the form of a pharmaceutical composition such as a tablet, capsule, granule, fine granule, powder, solution, syrup, suspending agent, emulsion, or elixir, and alternatively may be added to a food, chewing gum, or beverage and taken in the form of a general food or so-called a food for specified health use.

The dose of the composition of the present invention varies according to the age and body weight of the patient, degree of disease, and administration route. In normal cases, the doses of the strawberry-derived polyphenol and polysaccharide thickener are 50 to 500 mg and 50 to 500 mg a day, respectively, and the frequency of administration is one to three times a day.

The composition of the present invention is produced according to common procedure using an excipient such as starch, lactose, white sugar, mannit, carboxymethyl cellulose, cornstarch, or any inorganic salt. The composition of the present invention may further contain, in addition to the excipient, a binder, a disintegrating agent, a surfactant, a lubricant, a flow promoter, a flavoring agent, a coloring agent, and a perfume.

Specific examples of the binder include crystal cellulose, crystal cellulose-sodium carboxymethyl cellulose, methyl cellulose, hydroxypropyl cellulose, low substitution degree hydroxypropyl cellulose, hydroxypropylmethyl cellulose, hydroxypropylmethyl cellulose phthalate, hydroxypropylmethyl cellulose acetate succinate, sodium carboxymethyl cellulose, ethyl cellulose, carboxymethyl ethyl cellulose, hydroxyethyl cellulose, wheat starch, rice starch, corn starch, potato starch, dextrin, gelatinized starch, partially gelatinized starch, hydroxypropyl starch, pullulan, polyvinyl pyrrolidone, aminoalkyl methacrylate copolymer E, aminoalkyl methacrylate copolymer RS, methacrylic acid copolymer L, methacrylic acid copolymer, polyvinyl acetal diethylamino acetate, polyvinyl alcohol, agar, gelatin, white shellac, tragacanth, purified white sugar, and Macrogol.

Specific examples of the disintegrating agent include crystal cellulose, methyl cellulose, low substitution degree hydroxypropyl cellulose, carboxymethyl cellulose, calcium carboxymethyl cellulose, sodium carboxymethyl cellulose, sodium croscarboxymethyl cellulose, wheat starch, rice starch, corn starch, potato starch, partially gelatinized starch, hydroxypropyl starch, carboxymethyl starch sodium, and tragacanth.

Specific examples of the surfactant include soybean lecithin, sucrose fatty acid ester, polyoxyl stearate, poly(oxyethylene) hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glycerol monostearate, sodium lauryl sulfate, and Lauromacrogol.

Specific examples of the lubricant include, wheat starch, rice starch, corn starch, stearic acid, calcium stearate, magnesium stearate, hydrous silicon dioxide, light silicic anhydride, synthetic aluminium silicate, dried aluminium hydroxide gel, talc, magnesium aluminometasilicate, calcium hydrogen phosphate, anhydrous calcium hydrogen phosphate, sucrose fatty acid ester, wax, hydrogenated vegetable oil, and polyethylene glycol.

Specific examples of the flow promoter include, hydrous silicon dioxide, light silicic acid anhydride, dried aluminium hydroxide gel, synthetic aluminium silicate, and magnesium silicate.

When the composition of the present invention is administered in the form of a solution, syrup, suspending agent, emulsion, or elixir, the composition may contain a flavoring agent and a coloring agent.

EXAMPLES

The present invention is specifically described below with reference to examples, but the present invention will not be limited to these examples.

Preparation Example 1

Preparation and Separation of Hot Water Extract of Strawberry (1) Preparation of Extract Liquid 2.7 L of distilled water was added to 1.4 kg of pomace of strawberry fruit (Tochiotome; hereinafter the same shall apply), and autoclaved at 90° C. for 60 minutes, thereby achieving extraction. After cooling, the filtrate was separated from the residue and subjected to filtration under reduced pressure, the residue and container were washed with distilled water, and the washings were added to the filtrate to obtain 4.7 L of extract liquid.

(2) Separation 4.7 L of the hot water extract obtained as described in (1) was subjected to column chromatography using DIAION™ HP20 (Nippon Rensui Co.) (diameter 9.0 cm×length 19 cm), eluted sequentially with 6.0 L of water, 3.6 L of 10% aqueous ethanol solution, 3.6 L of 50% aqueous ethanol solution, and 3.6 L of 100% ethanol, and concentrated under reduced pressure, thereby obtaining the following polar fraction (fractions eluted with water and ethanol): fraction eluted with water (80.7 g), fraction eluted with a 10% aqueous ethanol solution (1.92 g), fraction eluted with a 50% aqueous ethanol solution (3.83 g), and fraction eluted with 100% ethanol (0.18 g).

The freeze-dried product of the fraction eluted with a 50% aqueous ethanol solution or a 10% aqueous ethanol solution was used as a strawberry polyphenol.

Aside from this, 80.7 g of the freeze-dried product of the fraction eluted with water was dissolved in a 70% aqueous ethanol solution, the deposited insoluble matter was filtered and washed with a 70% aqueous ethanol solution, and freeze-dried. The product thus obtained was used as strawberry pectin.

Preparation Example 2

Preparation of Hot Water Extract of Strawberry 1.8 L of distilled water was added to 304 g of strawberry pomace, and autoclaved at 90° C. for 60 minutes, thereby achieving extraction. After cooling, the filtrate was separated from the residue and subjected to filtration under reduced pressure, the residue and container were washed with distilled water, and the washings were added to the filtrate to obtain an extract liquid. The extract liquid thus obtained was freeze-dried.

Table 1 shows the moisture content of the strawberry pomace and the extraction efficiency (the value obtained when 600 mL of distilled water was added to 100 g of the strawberry pomace, and extracted once).

TABLE 1

|  | Content rate (%) | Extraction efficiency per wet weight (%) | Extraction efficiency per dry weight (%) |
|---|---|---|---|
| Strawberry pomace | 77.6 | 7.86 | 35.1 |

Preparation 3

Preparation of Hot Water Extract of Strawberry 2.4 L of 1% citric acid aqueous solution was added to 0.8 kg of strawberry pomace, and autoclaved at 90° C. for 60 minutes, thereby achieving extraction. After cooling, the filtrate was separated from the residue and subjected to filtration under reduced pressure, thereby obtaining an extract liquid.

Test Example 1

Assay of Polyphenol

The polyphenol in the test sample was assayed using the Folin-Denis method. The test sample was dissolved in water or a mixture of water and a small amount of ethanol, the hot water extract (freeze-dried product obtained in Preparation Example 2) and the fraction eluted with water obtained in Preparation Example 1 were adjusted to 200 μg/mL, and the fractions eluted with a 10% aqueous ethanol solution and a 50% aqueous ethanol solution obtained in Preparation Example 1 were adjusted to 50 μg/mL. 1.0 mL of Folin reagent was added to and mixed with 1.0 mL of the preparation, and after a lapse of 3 minutes or more, 1.0 mL of 10% sodium carbonate aqueous solution was added, and thoroughly mixed. After standing for one hour under shaded conditions, the absorbance at 760 nm was measured. Aside from this, blanks of the test samples were prepared in the same procedure except that water was used in place of the Folin reagent, and the blank values were deducted from the measured values.

The error becomes large if the polyphenol concentration is too high or too low. Therefore, the fraction eluted with water and the fraction eluted with a 50% aqueous ethanol solution which showed an absorbance out of the range of 0.3 to 0.5 were adjusted to 1500 μg/mL and 20 μg/mL, respectively, and measured again.

The values were calculated from the calibration curve, which had been prepared using chlorogenic acid as the reference material.

Polyphenol content (%)=[calculated value from the calibration curve (μg/mL)/test sample concentration (μg/mL)]× 100 The results are shown in Table 2.

TABLE 2

| Test sample | Polyphenol content |
|---|---|
| Hot water extract of strawberry | 5.77 |
| Fraction eluted with water | 0.96 |
| Fraction eluted with a 10% aqueous ethanol solution | 33.37 |
| Fraction eluted with a 50% aqueous ethanol solution | 63.73 |

Example 1

Anti-Obesity Test

Figure 2:
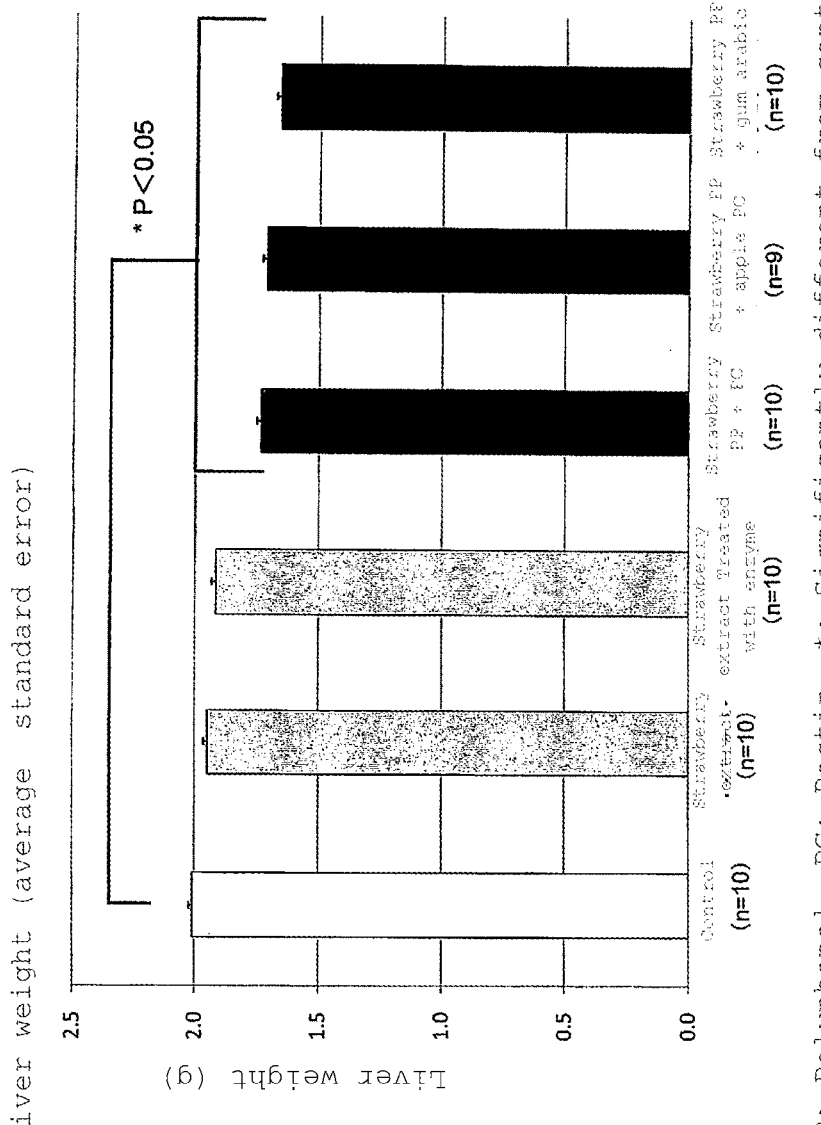
FIG. 2 is a graph showing liver weight measurements.

Purpose
(1) To verify the interaction of strawberry polyphenol and polysaccharide thickeners such as pectin on anti-obesity effect.
(2) To determine whether the hot water extract of strawberry has anti-obesity effect or not.
Method
(1) Test Sample
   (a) Hot Water Extract of Strawberry
     (i) Strawberry without enzyme treatment was suspended in a 0.5% citric acid aqueous solution, heated at 90° C. for 60 minutes, and then filtered.
     (ii) The strawberry with enzyme treatment was heated at 90° C. for 60 minutes, and then filtered.
   (b) Strawberry Polyphenol
     The fraction eluted with a 50% aqueous ethanol solution obtained in Preparation Example 1 (2) was used.
   (c) Strawberry Pectin
     The pectin obtained in Preparation Example 1 (2) was used.
   (d) Apple Pectin and Gum Arabic
     Apple-derived pectin (manufactured by Wako Pure Chemical Industries, Ltd.) and gum arabic (manufactured by Nacalai Tesque, Inc.) were purchased.
(2) Animal and Breeding
   ICR/Kwl mice (male, 5 weeks old) were bred with a high-fat, high-caloric feed (Quick Fat, manufactured by Nippon CLEA).
(3) Administration Method
   The administration was started on day 8 after initiation of breeding. Forced oral administration was continuously carried out 14 times.
(4) Test Groups
   The following six groups each containing ten animals were used.
   (a) Control group: water
   (b) Hot water extract of strawberry without enzyme treatment: 1000 mg/kg
   (c) Hot water extract of strawberry with enzyme treatment: 1000 mg/kg
   (d) Strawberry polyphenol+apple pectin: 100 mg/kg each
   (e) Strawberry polyphenol+gum arabic: 100 mg/kg, 800 mg/kg
   (f) Strawberry polyphenol+strawberry pectin: 100 mg/kg each
(5) Measurement
   The feed intake, water intake, and body weight were measured every day.
(6) Anatomy and Biochemical Test
   The animals were fasted one day before anatomy. The systemic blood was collected from the heart under ether anesthesia, centrifuged, and then the serum was stored at −80° C. In addition, the liver was extirpated, and its weight was measured. As the blood components, total cholesterol, HDL-cholesterol, triglyceride, and blood glucose level were measured.
(7) Statistical Processing
   After carrying out analysis of variance (ANOVA), $p<0.05$ by post hoc test was regarded as significant difference.
Conclusion
   The administration of the strawberry polyphenol and polysaccharide thickener (pectin and gum arabic) brought about very strong anti-obesity effect.
(1) Change of Body Weight
   The body weight gain was significantly inhibited in the group dosed with strawberry polyphenol+polysaccharide thickener. On days 4 and 5 after initiation of administration, the body weight gain was significantly inhibited in the group dosed with strawberry polyphenol+polysaccharide thickener, in comparison with the control group. The body weight gain was inhibited also by the hot water extract of strawberry without enzyme treatment. The strawberry treated with enzyme did not inhibited body weight gain. The results are shown in FIG. 1.
(2) Obesity Parameter
   The liver weight significantly decreased in the group dosed with strawberry polyphenol+polysaccharide thickener. The results are shown in FIG. 2.
Discussion
   It was found that the simultaneous intake of a strawberry polyphenol and a polysaccharide thickener brings about anti-obesity effect. The reason for this is likely that the strawberry polyphenol is more efficiently absorbed in the body by the polysaccharide thickener to bring about anti-obesity effect.

Example 2

Antiallergic Test

Purpose
   To determine whether the strawberry polyphenol has antiallergic effect or not.
Method
(1) Test Sample
   (a) Strawberry Polyphenol
     The fraction eluted with a 50% aqueous ethanol solution obtained in Preparation 1 (2) was used.
   (b) Strawberry Pectin
     The pectin obtained in Preparation 1 (2) was used.
(2) Animal and Breeding
   BALB/c mice (male, 5 weeks old) were bred with a feed CRF-1 for rats, mice, and hamsters.
(3) Grouping, Initial Immunity, and Secondary Immunization
   (a) On days 6 and 10 after initiation of breeding, 0.2 mL per animal of 0.1 mg/mL OVA-alum solution (a solution containing equal amounts of 0.2 mg/mL OVA and alum gel) was intraperitoneally administered (OVA 20 µg/mouse).
   (b) For seven days from day 18 after initiation of breeding, 10 µL per animal of 34 mg/mL OVA was nasotracheally administered 1 hour and 2 hours after administration of the test sample.
   (c) Test Group
     (i) Unsensitized control
     (ii) Control (distilled water was orally administered)
     (iii) Strawberry polyphenol 100 mg/kg+strawberry pectin 60 mg/kg
     (iv) Strawberry polyphenol 200 mg/kg+strawberry pectin 60 mg/kg Oral administration of (ii), (iii), and (iv) was carried out every day from 6 days after initiation of breeding.

(4) Anatomy and Biochemical Test

On day 27 after initiation of breeding, blood was collected from the heart under ether anesthesia (EDTA was used). The OVA-specific IgE and IgG1 in the serum were measured. The spleen was extirpated and weighed.

(5) Statistical Processing

All the data are expressed as average±standard error. Significance level of less than 5% in Thompson test was removed. The animal whose data was removed using the Thompson test was not studied for other items. T test was carried out between the unsensitized control and control. The significance level was less than 5%. The analysis of variance (ANOVA) was carried out between the control and sample. The significance level was less than 5%. When a significant difference was found in ANOVA, Dunnett test was carried out.

Result

The spleen weight was evidently lower in group dosed with the strawberry polyphenol. The OVA-IgE was slightly lower in the group dosed with 100 mg/kg of the strawberry polyphenol. The OVA-IgG1 was evidently lower in the group dosed with 100 mg/kg of the strawberry polyphenol.

On the other hand, the OVA-IgE was slightly higher in the group dosed with 200 mg/kg of the strawberry polyphenol, and the OVA-IgG1 was higher than the group dosed with 100 mg/kg.

Figure 3:
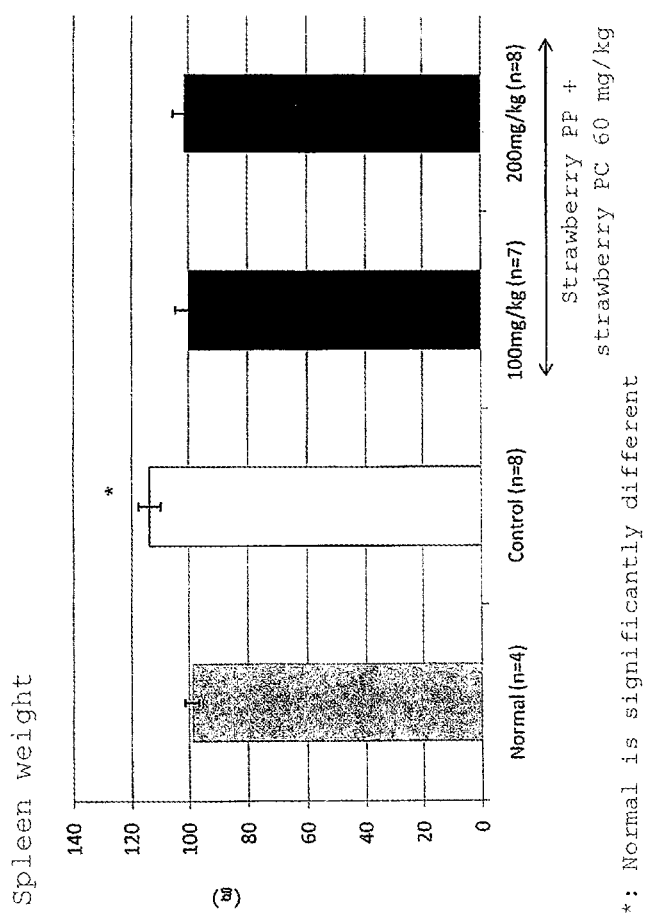
FIG. 3 is a graph showing spleen weight measurements.
Figure 4:
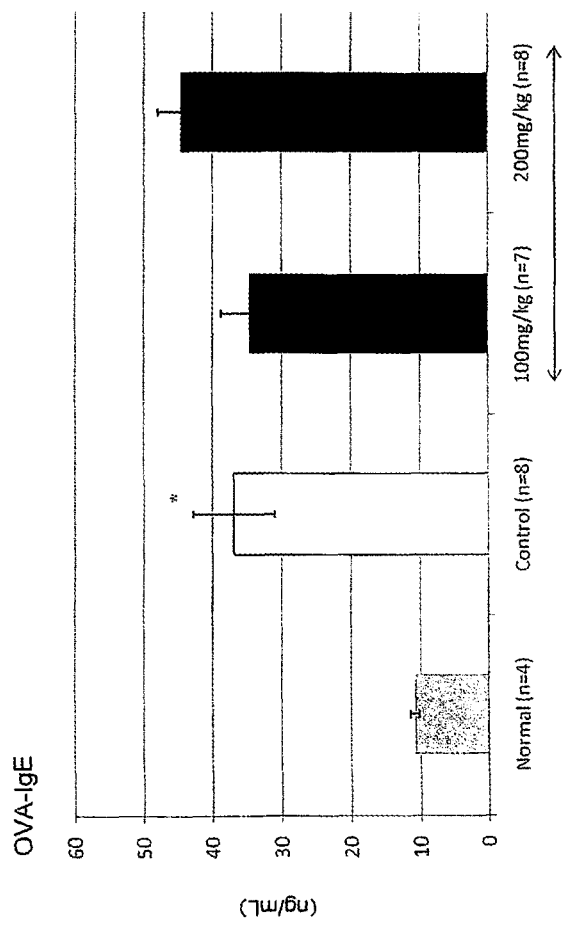
FIG. 4 is a graph showing OVA-IgE measurements.
Figure 5:
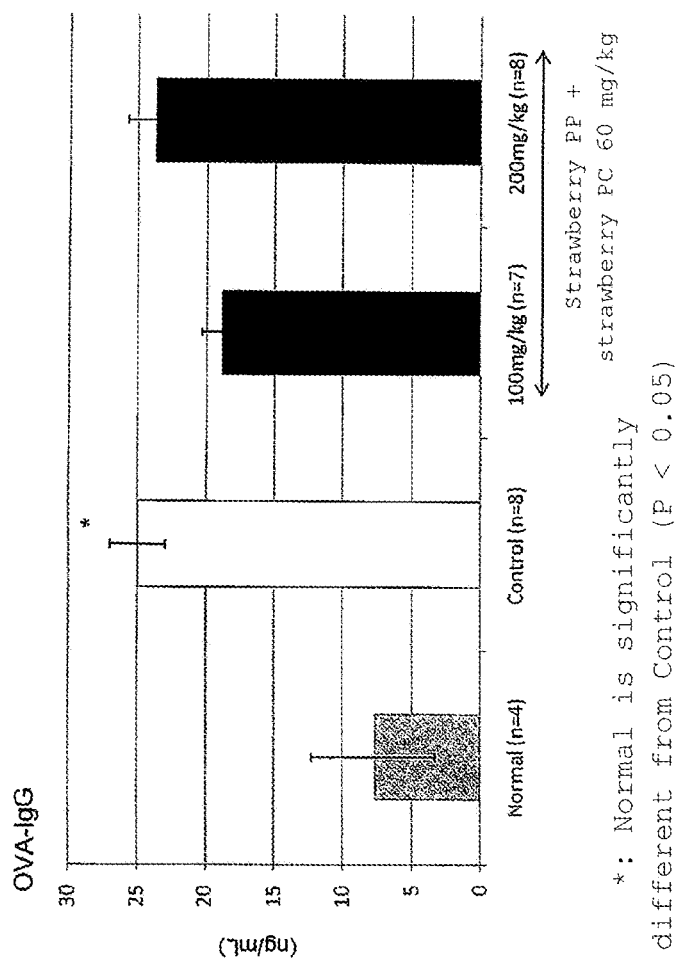
FIG. 5 is a graph showing OVA-IgG1 measurements.

The measurements of the spleen weight, OVA-IgE, and OVA-IgG1 are shown in FIGS. 3, 4, and 5, respectively.

Conclusion

The possibility that the strawberry polyphenol has anti-allergic effect was suggested, and the effect was considered to be achieved by the administration of an optimum dose.

Example 3

Cytokine Production Test

Abstract

Normal human epidermal keratinocytes were treated with phorbol 12-myristate 13-acetate (PMA), which is a stimulant, and a strawberry-derived fraction, and the amounts of production of three cytokines, or interleukin 1β, 6, and 8 (IL-1β, IL-6, and IL-8) were measured, thereby evaluating the anti-inflammatory effect of the test sample.

Material and Method (1) Cells

Asian-derived normal human keratinocytes (manufactured by NHEK manufactured by DS Pharma Biomedical Co., Ltd.) were the third or higher passage cultured on a serum-free medium for normal human keratinocytes (manufactured by DS Pharma Biomedical Co., Ltd.).

(2) Test Samples and Reagent

The test sample was the freeze-dried product of the fraction eluted with a 10% aqueous ethanol solution obtained in Preparation 1 (2).

The cell stimulant was phorbol 12-myristate 13-acetate (PMA, manufactured by Sigma-Aldrich), and the MTT reagent (manufactured by Nacalai Tesque, Inc.) and SDS-HCl reagent were used for the evaluation of the survival rate. In addition, READY-SET-GO! Human Interleukin-1 beta (manufactured by eBioscience), READY-SET-GO! Human Interleukin-6 (manufactured by eBioscience), and IL-8/NAP-1 Immunoassay Kit (manufactured by Biosource) were used for the evaluation of the cytokine-producing capacity.

(3) Method (a) Cell Survival Assay (Toxicity Test)

NHEK cultured in a flask was adjusted to $5.0 \times 10^4$ cells/mL, and seeded on a 96 well plate in a volume of 200 μL (final concentration: $1.0 \times 10^4$ cells/well). After culturing at 37° C. for 24 hours, 25 μL of PMA adjusted to 100 ng/mL (final concentration: 10 ng/mL) and 25 μL of the test sample adjusted to 100, 1000 μg/mL (final concentration: 10,100 μg/mL) were added. After culturing for 48 hours, the culture medium was collected, and stored at −80° C. for Enzyme Linked-Immuno-Sorbent Assay (ELISA). 80 μL of new culture medium and 20 μL of MTT reagent were added to the cells, and cultured for 3 to 5 hours, and 150 μL of the SDS-HCl reagent was added. After culturing for 18 to 20 hours, the absorbance at 570 nm was measured.

(b) Measurement of the Amount of Cytokine Production by Enzyme Linked Immuno Sorbent Assay (ELISA)

The culture medium stored at −80° C. was measured for the amount of cytokine by the ELISA method.

(i) Biosource (IL-8) Pre-Coated Type

The unfrozen culture medium was diluted three times with Standard Diluent Buffer, 50 μL of the dilution was added to a 96-well plate processed with IL-8 antibody together with a standard solution, and 50 μL of Biotin Conjugate was further added and allowed to react for 90 minutes at room temperature. After removing the solution, the well was washed with Wash Buffer four times, and then 100 μL of Streptavidin-HRP Working Solution was added and allowed to react for 30 minutes. After removing the solution, the well was washed with Wash Buffer five times, and then 100 μL of Stabilized Chromogen was added and allowed to react for 10 to for 15 minutes. 100 μL of Stop Solution was added to halt the reaction, and the absorbance at 450 nm was measured. A calibration curve was prepared by plotting the absorbance of the standard solution, and the amount of IL-8 production was calculated.

(ii) eBioscience (IL-1β, 6) Non-Coated Type

100 μL of Capture Antibody diluted with Coating Buffer was added to a 96 well maxisorp plate, and cultured overnight at 4° C. After removing the solution, the well was washed with Wash Buffer five times, and then 200 μL of Assay Diluent was added and allowed to react for 1 hour at room temperature. After removing the solution, the well was washed with Wash Buffer five times, and then 100 μL of the unfrozen culture medium diluted ten and five times was added together with the standard solution, and allowed to react for 2 hours at room temperature. After removing the solution, the well was washed with Wash Buffer five times, and then 100 μL of Detection Antibody was added and allowed to react for 1 hour at room temperature. After removing the solution, the well was washed with Wash Buffer five times, and then 100 μL of Avidin-HRP was added and allowed to react for 30 minutes at room temperature. After removing the solution, the well was washed with Wash Buffer seven times, and then 100 μL of Substrate Solution was added and allowed to react for 10 to for 15 minutes. 100 μL of Stop Solution was added to halt the reaction, and the absorbances at 450 and 570 nm were measured. A calibration curve was prepared by plotting the absorbance of the standard solution, and the amounts of 1L-1β and 6 production were calculated individually.

Result (1) Amount of Cytokine Production

The measured amount of cytokine production was multiplied by the dilution ratio of the cell supernatant and expressed as the amount of production (pg/mL), and then multiplied by the result of the cell survival assay and expressed as percentage taking the control as 100%, thereby allowing the comparison between equal numbers of cells. In this manner the influences of the PMA and test sample on the cytokine production were evaluated.

(a) Interleukin 1β

The amount of 1L-1β production was small, so that 1L-1β was not detected by the present method using a 10-fold dilution of the cell supernatant.

(b) Interleukin 6

Figure 6:
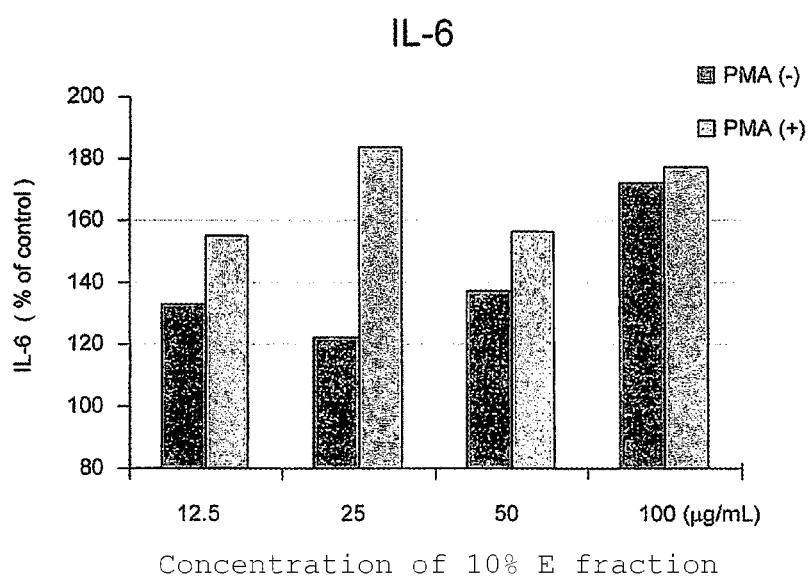
FIG. 6 is a graph showing the amount of IL-6 production.

Comparison were made between an equal number of cells, and the production of a small amount of IL-6 was found under the PMA(+) conditions (Table 3 and FIG. 6). In addition, the production by the test sample was found under the PMA(−) and PMA(+) conditions.

TABLE 3

| | PMA (−) | | PMA (+) | | |
|---|---|---|---|---|---|
| Concentration (μg/mL) | Amount of production (pg/mL) | (−) con. as 100 (%) | Amount of production (pg/mL) | (−) con. as 100 (%) | (+) con. as 100 (%) |
| Control | 107 | 100.0 | 89 | 181.9 | 100.0 |
| 12.5 | 111 | 132.8 | 131 | 281.6 | 154.8 |
| 25 | 98 | 122.3 | 163 | 334.4 | 183.8 |
| 50 | 97 | 137.2 | 143 | 284.4 | 156.3 |
| 100 | 89 | 171.9 | 152 | 322.6 | 177.3 |

(c) Interleukin 8

Figure 7:
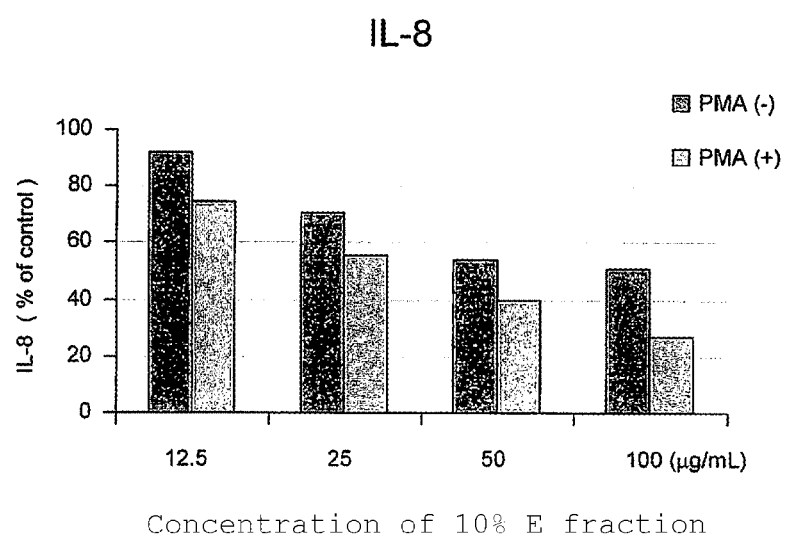
FIG. 7 is a graph showing the amount of IL-8 production.

The amount of IL-8 production was twenty times or more higher than the amount of IL-1β or 6 production (Table 4 and FIG. 7).

The addition of PMA brought about marked production of IL-8. The test sample inhibited the production in a concentration-dependent manner.

TABLE 4

| | PMA (−) | | PMA (+) | | |
|---|---|---|---|---|---|
| Concentration (μg/mL) | Amount of production (pg/mL) | (−) con. as 100 (%) | Amount of production (pg/mL) | (−) con. as 100 (%) | (+) con. as 100 (%) |
| Control | 1992 | 100.0 | 3173 | 346.9 | 100.0 |
| 12.5 | 1472 | 92.0 | 2234 | 258.3 | 74.4 |
| 25 | 1065 | 70.9 | 1762 | 193.4 | 55.7 |
| 50 | 712 | 53.7 | 1301 | 138.9 | 40.0 |
| 100 | 490 | 50.6 | 811 | 92.3 | 26.6 |

Discussion

Of the three cytokines studied herein, IL-6 was produced in a small amount by the addition of the test sample, but the amount was far smaller than the amount of IL-8 production, indicating that the inflammatory action is likely very weak. On the other hand, the production of IL-8 was markedly inhibited by the addition of the test sample. The activity was observed under both the PMA(−) conditions and (+) conditions, indicating a high level of anti-inflammatory or antiphlogistic effect.

Example 4

Melanin Production Inhibition Test

Abstract

Human melanoma cells (HMVII) were treated with a strawberry-derived substance, and the amount of melanin production was compared with that of a negative control, thereby studying the production inhibitory effect (whitening effect).

Material and Method (1) Cells

Human melanoma cells (HMVII) were the third or higher passage cultured in a culture solution of a Ham F-12 culture medium (manufactured by Nissui Pharmaceutical Co., Ltd.) containing 10% FBS, mixed with 0.5% penicillin-streptomycin (manufactured by Gibco).

(2) Test Sample

The test samples were the freeze-dried products of the hot water extract obtained in Preparation 1 (1) and the fractions eluted with 10% and 50% aqueous ethanol solutions obtained in Preparation 1 (2).

(3) Method (a) Amount of Melanin Production

960 μL of human cells HMVII cultured in Ham F-12 culture medium containing 10% FBS was seeded on a 24-well plate containing 10% FBS to give a final concentration of $1.0 \times 10^5$ cells/well (seeding concentration: $1.04 \times 10^5$ cells/mL), and cultured for 24 hours in a $CO^2$ incubator. 20 μL of melanin production hormone (α-MSH) adjusted to a final concentration of 100 ng/mL (addition concentration: 5.0 μg/mL) and 20 μL of test sample adjusted to 10 μg/mL (500 μg/mL) or 100 μg/mL (5000 μg/mL) were added, and cultured for 72 hours. The culture medium was removed, washed with PBS, and then 100 μL of a trypsin EDTA solution was added thereby removing the cells from the plate, and 900 μL of 1N sodium hydroxide aqueous solution was added. The cells were allowed to stand at room temperature for 20 to 24 hours thereby causing cytolysis, and then the melanin content was measured at an absorbance of 475 nm.

(b) Cell Survival Rate

In order to correct the influence of the test sample on the cell survival rate (proliferation rate), the survival rate was calculated by the MTT method using the control as a standard, and the measured melanin value was multiplied by the survival rate. 160 was seeded on a 96-well plate at $2.0 \times 10^4$ cells/well ($1.25 \times 10^5$ cells/mL), and cultured for 24 hours. 20 μL of melanin production hormone (α-MSH) adjusted to a final concentration of 100 ng/mL (1.0 μg/mL) and 20 μL of test sample adjusted to 10 μg/mL (100 μg/mL) or 100 μg/mL (1000 μg/mL) were added, and cultured for 72 hours. The old culture medium was removed, 80 μL of new culture medium and 20 μl of MTT reagent were added, and cultured for 3 to 5 hours. 150 μL of SDS-HCl reagent was further added, cultured for 18 to 20 hours, and then the absorbance at 570 nm was measured.

Result

Figure 8:
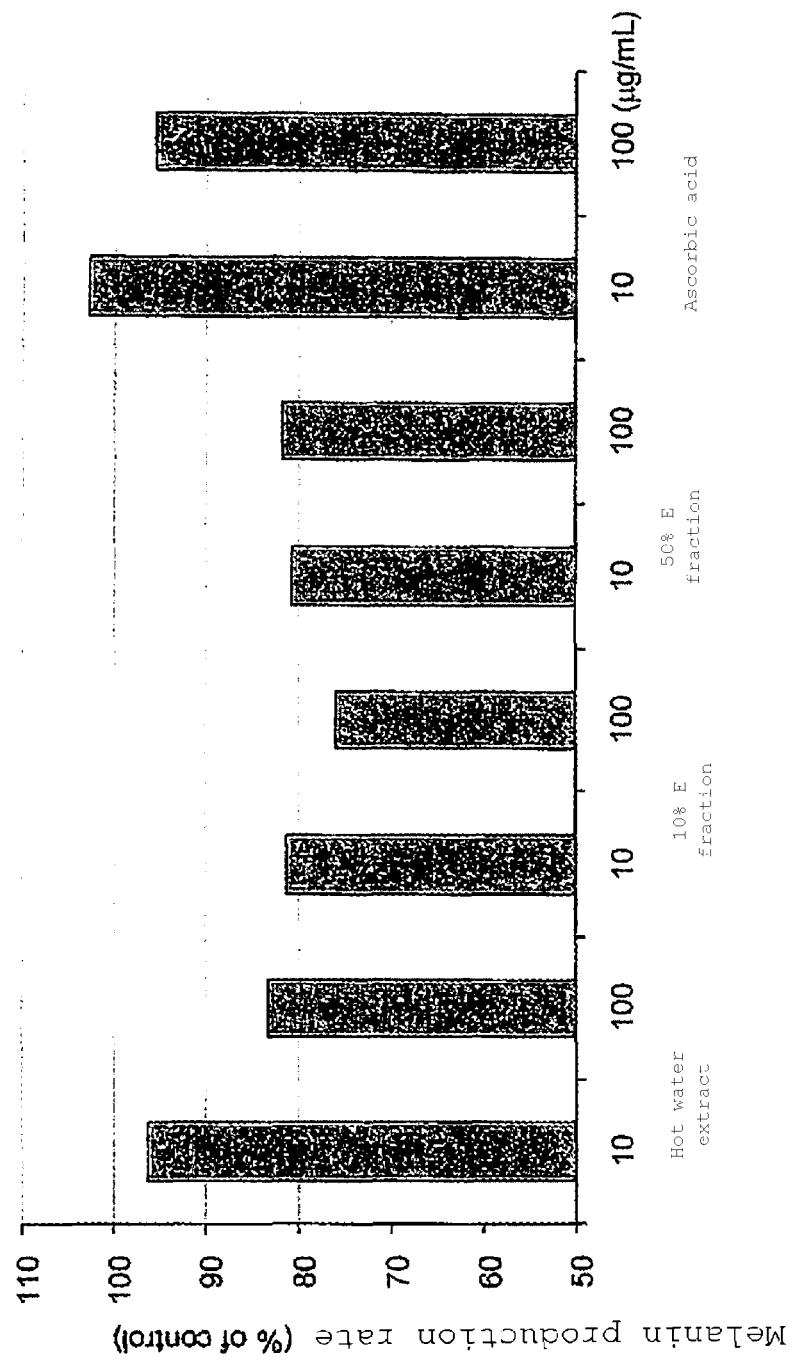
FIG. 8 is a graph showing the result of melanin production inhibitory test using HMVII cells.

According to the results of the MTT test, the addition of the hot water extract of strawberry and its fractions to the HMVII cells generally increased the survival rate, indicating that the sample has cell growth-promoting activity. Therefore, even when the measured amount of melanin production of the sample was higher than that of the control, the sample value became lower than the control value after correction with the survival rate, indicating that the sample has melanin production inhibitory activity (Table 5 and FIG. 8).

TABLE 5

| Test sample | Concentration (μg/mL) | Melanin production rate (%) | Survival rate (%) | Melanin production rate after correction of survival rate (%) |
|---|---|---|---|---|
| Control | | 100 | 1.00 | 100 |
| Hot water extract | 10 | 100.52 | 1.04 | 96.30 |
| | 100 | 102.09 | 1.22 | 83.35 |
| Fraction eluted with 10% ethanol | 10 | 100 | 1.23 | 81.26 |
| | 100 | 97.03 | 1.28 | 75.89 |
| Fraction eluted with 50% ethanol | 10 | 97.91 | 1.21 | 80.75 |
| | 100 | 96.86 | 1.18 | 81.81 |
| Ascorbic acid | 10 | 97373 | 0.95 | 102.74 |
| | 100 | 94.76 | 0.99 | 95.60 |

Example 5

Melanin Production Inhibition Test

Abstract

The mouse melanoma cells B16F1 were treated with a strawberry-derived substance, and the amount of melanin production was compared with that of the negative control, thereby evaluating the production inhibitory effect (whitening effect) of the substance.

Material and Method (1) Cells

Mouse melanoma cells B16F1 were the third or higher passage cultured in Dulbecco's Modified Eagle Medium (D-MEM) containing 10% FBS (manufactured by Nissui Pharmaceutical Co., Ltd.) mixed with 0.5% penicillin-streptomycin (manufactured by Gibco).

(2) Test Sample

The test samples were the freeze-dried products of the hot water extract obtained in Preparation 1 (1) and the fractions eluted with 10% and 50% aqueous ethanol solutions obtained in Preparation 1 (2).

(3) Method (a) Amount of Melanin Production

960 μL of mouse cells B16F1 cultured in D-MEM culture medium containing 10% FBS was seeded on a 24-well plate to give a final concentration of $1.0 \times 10^5$ cells/well (seeding concentration: $1.04 \times 10^5$ cells/mL), and cultured for 24 hours in a $CO^2$ incubator. 20 μL of melanin production hormone (α-MSH) adjusted to a final concentration of 100 ng/mL (addition concentration: 5.0 μg/mL) and 20 μL of test sample adjusted to 10 μg/mL (500 μg/mL) or 100 μg/mL (5000 μg/mL) were added, and cultured for 72 hours. The culture medium was removed, washed with PBS, and then 100 μL of a trypsin EDTA solution was added thereby removing the cells from the plate, and 900 μL of 1N sodium hydroxide aqueous solution was added. The cells were allowed to stand at room temperature for 20 to 24 hours thereby causing cytolysis, and then the melanin content was measured at an absorbance of 475 nm.

(b) Cell Survival Rate

In order to correct the influence of the test sample on the cell survival rate (proliferation rate), the survival rate was calculated by the MTT method using the control as a standard, and the measured melanin value was multiplied by the survival rate. 160 μL was seeded on a 96-well plate at $2.0 \times 10^4$ cells/well ($1.25 \times 10^5$ cells/mL), and cultured for 24 hours. 20 μL of melanin production hormone (α-MSH) adjusted to a final concentration of 100 ng/mL (1.0 μg/mL) and 20 μL of test sample adjusted to 10 μg/mL (100 μg/mL) or 100 μg/mL (1000 μg/mL) were added, and cultured for 72 hours. The old culture medium was removed, 80 μL of new culture medium and 20 μL of MTT reagent were added, and cultured for 3 to 5 hours. 150 μL of SDS-HCl reagent was further added, cultured for 18 to 20 hours, and then the absorbance at 570 nm was measured.

Result

Figure 9:
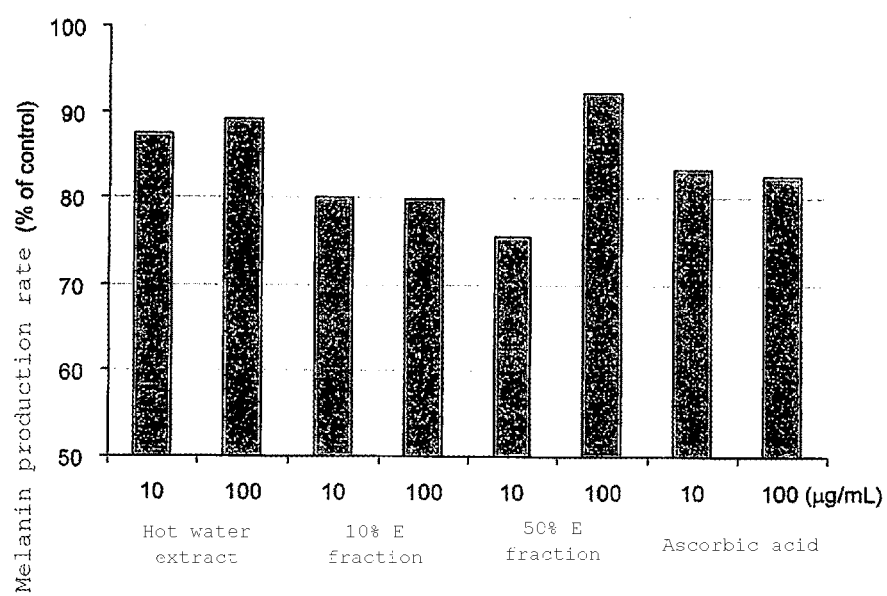
FIG. 9 is a graph showing the result of melanin production inhibitory test using B16F1 cells.

According to the results of the MTT test, the addition of the hot water extract of strawberry and its fractions to the B16F1 cells brought about melanin production inhibitory activity in all the samples at the same level with the positive control (Table 6 and FIG. 9).

TABLE 6

| Test sample | Concentration (μg/mL) | Melanin production rate (%) | Survival rate (%) | Melanin production rate after correction of survival rate (%) |
|---|---|---|---|---|
| Control | | 100 | 1.00 | 100 |
| Hot water extract | 10 | 94.31 | 1.08 | 87.65 |
| | 100 | 94.86 | 1.06 | 89.21 |
| Fraction eluted with 10% ethanol | 10 | 93.76 | 1.17 | 80.08 |
| | 100 | 92.65 | 1.16 | 79.96 |
| Fraction eluted with 50% ethanol | 10 | 93.76 | 1.24 | 75.44 |
| | 100 | 88.79 | 0.96 | 92.38 |
| β arbutin | 10 | 95.41 | 1.14 | 83.48 |
| | 100 | 93.76 | 1.14 | 82.52 |

Example 6

Tyrosinase Activity Inhibition Test

Inhibition of the biochemical reaction intermediated by tyrosinase during intracellular production of melanin by the test samples was studied in vitro.

Material and Method (1) Test Samples

The test samples were the freeze-dried products of the hot water extract obtained in Preparation 1 (1) and the fractions eluted with 10% and 50% aqueous ethanol solutions obtained in Preparation 1 (2).

(2) Method 0.5 mL of substrate (DOPA) solution adjusted to the final concentration of 0.03% with a phosphoric acid buffer was mixed with 0.5 mL of test sample solution prepared using a phosphoric acid buffer, and cooled on ice. 0.5 mL of tyrosinase solution adjusted to the final concentration of 45 U/mL with a phosphoric acid buffer was added to the mixture, incubated at 25° C. for 5 minutes, and then the absorbance at 475 nm was measured. The reaction rate (activity) of tyrosinase was calculated from the difference of the absorbance. In order to eliminate the influence of the color of the test sample, the absorbance of a mixture containing a phosphoric acid buffer in place of the tyrosinase solution was measured, thereby correcting the absorbance.

Result

Figure 10:
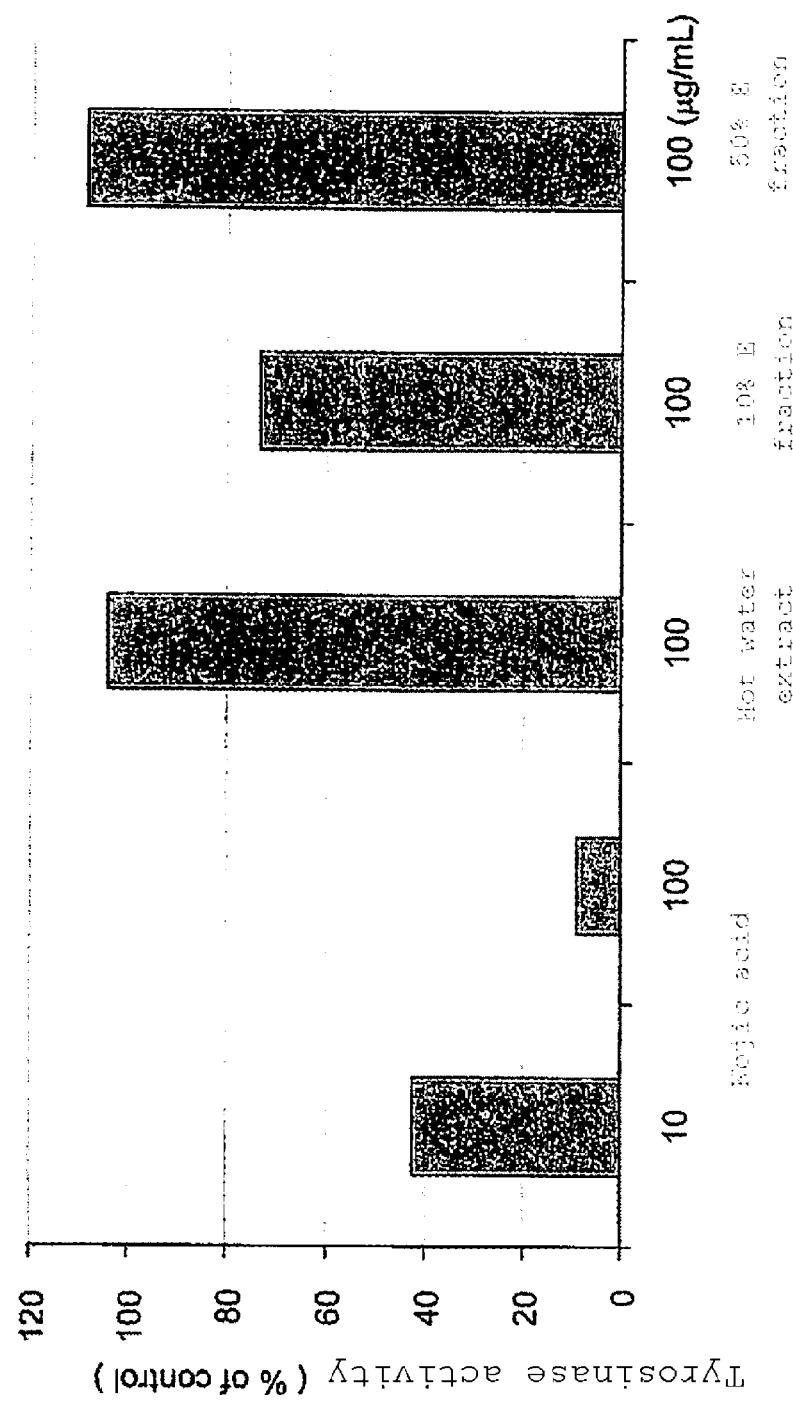
FIG. 10 is a graph showing the result of tyrosinase activity inhibition test.

The hot water extract and the fraction eluted with a 50% aqueous ethanol solution showed inhibitory effects against melanin production in Example 5, while showed no inhibitory effect against tyrosinase. This fact disproves the theory that inhibitory effect against tyrosinase brings about inhibition of melanin production, and suggests the possibility of a whitening agent with a new mechanism. On the other hand, the fraction eluted with a 10% ethanol solution showed weak tyrosinase inhibition activity (Table 7 and FIG. 10). As described in Example 5, this fraction also showed an inhibitory effect against melanin production, suggesting that the fraction has a weak inhibitory effect against tyrosinase and an inhibitory effect against melanin production based on a certain mechanism other than tyrosinase inhibition.

TABLE 7

| | | Test sample | | | |
|---|---|---|---|---|---|
| | Control | Kojic acid | Hot water extract | Fraction eluted with 10% ethanol | Fraction eluted with 50% ethanol |
| Concentration (μg/mL) | | 10 | 100 | 100 | 100 |
| Reaction rate (%) | 100 | 42.35 | 8.71 | 104.24 | 73.75 | 108.56 |

Example 7

Second Anti-Obesity Test

Figure 11:
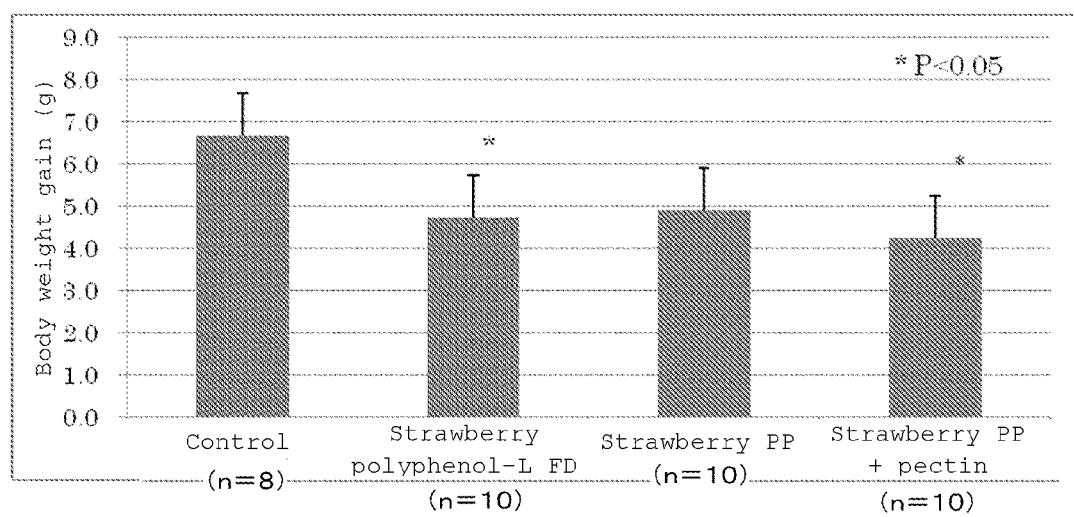
FIG. 11 is a graph showing the weight gain.
Figure 12:
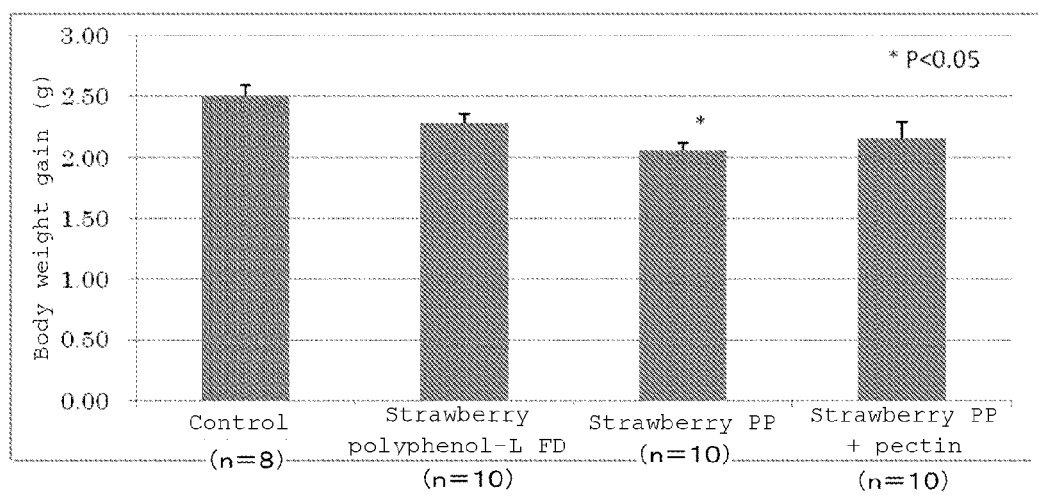
FIG. 12 is a graph showing liver weight measurements.
Figure 13:
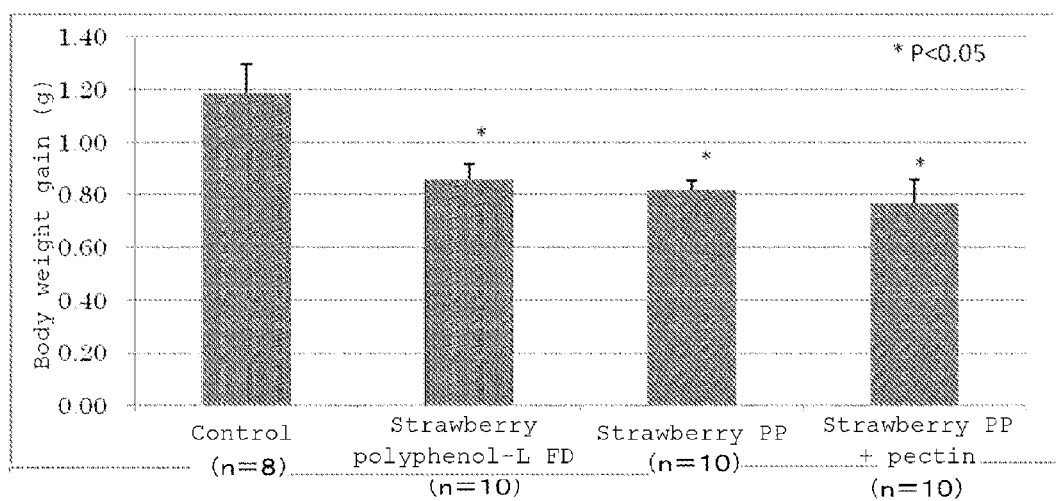
FIG. 13 is a graph showing measurements of weight of adipose tissues around epididymis.

Purpose
(1) To verify reproducibility of anti-obesity effect.
(2) To clarify the mechanism at mRNA level.
Method
(1) Test Sample
 (a) Hot Water Extract of Strawberry (Strawberry Polyphenol-L FD)
  (i) Strawberry without enzyme treatment was suspended in 0.5% citric acid aqueous solution, heated at 90° C. for 60 minutes, and then filtered.
  (ii) Strawberry with enzyme treatment was heated at 90° C. for 60 minutes, and then filtered.
 (b) Strawberry Polyphenol (Strawberry PP)
  The fraction eluted with a 50% aqueous ethanol solution obtained in Preparation Example 1 (2) was used.
 (c) Apple Pectin
  Apple-derived pectin was purchased from Wako Pure Chemical Industries, Ltd.
(2) Animal and Breeding
 ICR/KwI mice (male, 5 weeks old) were bred with a high-fat, high-caloric feed (Quick Fat, manufactured by Nippon CLEA).
(3) Administration Method
 The administration was started on day 8 after initiation of breeding. Forced oral administration was continuously carried out 14 times (once a day for two weeks).
(4) Test Groups
 The following four groups each containing ten animals were used.
  (a) Control group: water
  (b) Hot water extract of strawberry without enzyme treatment (strawberry polyphenol-L FD): 1000 mg/kg
  (c) Strawberry polyphenol (strawberry PP)=100 mg/kg
  (d) Strawberry polyphenol+apple pectin: 100 mg/kg each (5) Measurement
 The feed intake, water intake, and body weight were measured every day. In the control group, the body weight of two animals did not evidently increase, so that they were removed from the data analysis (the body weight of other animals increased by about 6.5 g, but the body weight of the removed two animals increased by only 3.4 g).
(6) Anatomy and Biochemical Test
 The animals were fasted one day before anatomy. The systemic blood was collected from the heart under ether anesthesia, centrifuged, and then the serum was stored at −80° C. In addition, the liver and adipose tissues around epididymis were extirpated, and weighed. mRNA was extracted from the liver, and cDNA was prepared therefrom.
(7) Gene Analysis
 The ACO gene (β oxidation-related gene) in the liver was measured by semi-quantitative measurement, using β actin as the internal standard.
(8) Statistical Processing
 ANOVA and Dannett test were carried out.
Conclusion
 The administration of the strawberry polyphenol brought about very strong anti-obesity effect.
(1) Change of Body Weight
 The body weight gain was significantly inhibited in the group dosed with strawberry polyphenol-L FD and the group dosed with strawberry PP+pectin. The body weight gain was inhibited also in the group dosed only with strawberry PP alone. The results are shown in FIG. 11.
(2) Liver Weight
 All the groups showed lower values than the control, and the group dosed with strawberry PP showed a significantly lower value. The results are shown in FIG. 12.
(3) Weight of Adipose Tissues Around Epididymis
 All the groups had a lower weight of the adipose tissues around epididymis than the control. The results are shown in FIG. 13.
(4) Expression of ACO Gene in Liver
 No difference was found by semi-quantitative measurement between the control and the test group dose with strawberry PP+pectin.
Discussion
 The polyphenol fraction of strawberry is considered to have anti-obesity effect.

Example 8

Third Anti-Obesity Test

Purpose
 To further study the above-described second anti-obesity test. It is reported that knockout of the gene inhibiting PPARγ activation brought about fat accumulation in the bone marrow, and that administration of a PPARγ antagonist to diabetic model mice inhibited PPARγ activation in the bone marrow. These facts suggest that inhibition of PPARγ activation can be evaluated using bone marrow cells.
Method
(1) Test Sample
 The same sample as the second anti-obesity test was used.
(2) Animal and Breeding
 ICR/KwI mice (male, 5 weeks old) were bred with a normal feed or a high-fat, high-sucrose feed, giving free access to water.
(3) Administration Method
 Administration was started on day 24 after initiation of breeding. Forced oral administration was carried out for three consecutive days.

(4) Test Groups

The following three groups each containing four animals were used.
(a) Normal feed
(b) High-fat, high-sucrose feed (control)
(c) High-fat, high-sucrose feed+strawberry PP: 200 mg/kg+pectin: 100 mg/kg (5) Gene Analysis Bone marrow cells were collected, and the aP2 gene (a downstream gene of PPARγ) was semi-quantitatively measured.

Conclusion

Figure 14:
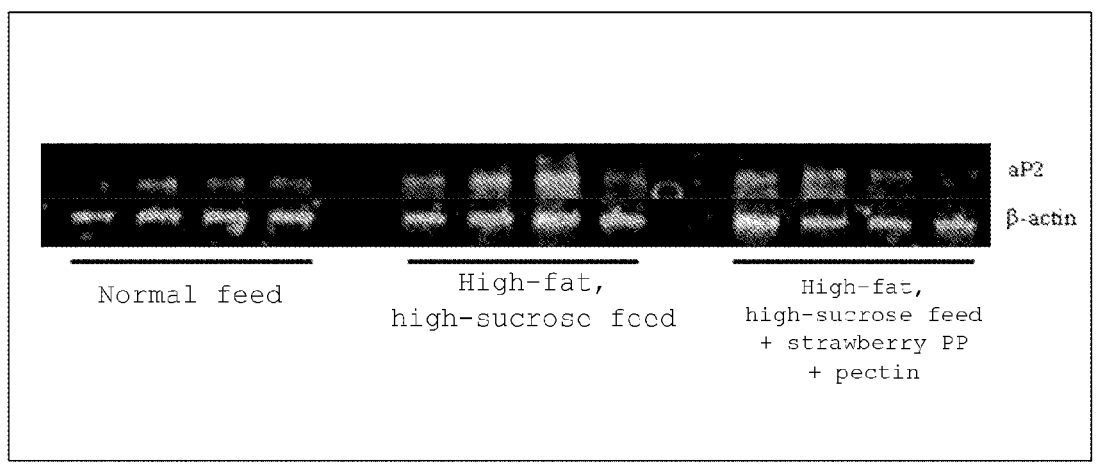
FIG. 14 is a graph showing the gene expression.

The aP2 gene expression was not higher in the group dosed with strawberry PP+pectin in comparison with the control. The result is shown in FIG. 14, suggesting the possibility that the inhibition of PPARγ activation suppresses the differentiation of adipocytes and fat accumulation.

Discussion

The anti-obesity effect of strawberry is likely brought about by suppression of differentiation of adipocytes and fat accumulation.

It is reported that knockout of the PPARγ gene causes the increase of the liver weight. In the second anti-obesity test, β oxidation in the liver was not detected at the gene level, but the decrease of the liver weight suggests that β oxidation may be also responsible for the anti-obesity effect.

The invention claimed is:

1. An anti-inflammatory composition for external use, comprising a fraction obtained by subjecting a hot water extract of strawberry to adsorption chromatography using an aromatic synthetic absorbent, removing the fractions passing through the column and fractions eluted with water, and then eluting with a 5 to 15% aqueous ethanol solution.

2. A melanin production inhibitor composition for external use, comprising a fraction obtained by subjecting a hot water extract of strawberry to adsorption chromatography using an aromatic synthetic absorbent, removing the fractions passing through the column and fractions eluted with water, and then eluting with a 5 to 15% aqueous ethanol solution.

3. An anti-obesity composition for oral administration comprising a fraction obtained by subjecting a hot water extract of strawberry to adsorption chromatography using an aromatic synthetic absorbent, removing the fractions-passing through the column- and fractions eluted with water and fractions eluted with a less than 40% aqueous ethanol solution, and then eluting with a 40 to 60% aqueous ethanol solution; wherein the composition comprises a strawberry-derived polyphenol and a polysaccharide thickener.

4. The composition of claim 3 wherein the polysaccharide thickener is strawberry-derived pectin.

* * * * *